United States Patent [19]

Reusser et al.

[11] Patent Number: 4,491,563

[45] Date of Patent: Jan. 1, 1985

[54] PROCESS FOR DEODORIZING A PARAFFINIC HYDROCARBON FEEDSTOCK

[75] Inventors: Robert E. Reusser; Timothy P. Murtha; Elizabeth A. Todd, all of Bartlesville, Okla.

[73] Assignee: Phillips Petroleum Company, Bartlesville, Okla.

[21] Appl. No.: 448,878

[22] Filed: Dec. 10, 1982

[51] Int. Cl.³ .................. C07C 7/12; C01B 17/16; B01J 8/02

[52] U.S. Cl. .................. 422/5; 423/230; 423/245; 585/820

[58] Field of Search .......... 422/4, 5; 502/65, 74, 502/406; 423/230, 245 S; 55/75; 260/702, 701; 585/820; 203/29, 31, 32, DIG. 16

[56] References Cited

U.S. PATENT DOCUMENTS

| | | | |
|---|---|---|---|
| 2,037,790 | 4/1936 | Ipatieff | 423/230 X |
| 3,078,321 | 2/1963 | Van Pool et al. | |
| 3,116,970 | 1/1964 | Stoep et al. | 423/230 X |
| 3,322,843 | 5/1967 | Frandolig et al. | 585/802 |
| 3,445,542 | 5/1969 | Bunn, Jr. et al. | |
| 3,523,772 | 8/1970 | Leaman et al. | 502/74 X |
| 3,629,356 | 12/1971 | Nakayama | |
| 4,122,125 | 10/1978 | Murtha et al. | 502/74 X |
| 4,153,671 | 5/1979 | Clements et al. | 423/245 S X |
| 4,189,405 | 2/1980 | Knapton et al. | 502/74 X |
| 4,217,248 | 8/1980 | Murtha | 502/74 X |
| 4,218,307 | 8/1980 | McDaniel | 502/65 |
| 4,221,677 | 9/1980 | Vasalos et al. | 502/65 |
| 4,351,980 | 9/1982 | Reusser et al. | 585/820 |
| 4,369,130 | 1/1983 | Bertolacini et al. | 502/65 |
| 4,371,507 | 2/1983 | Farha, Jr. et al. | 423/230 |
| 4,423,280 | 12/1983 | Dessau | 585/820 X |

OTHER PUBLICATIONS

Comprehensive Inorganic Chemistry, J. C. Bailar, Jr., H. J. Emeleus, Nyholm, and Trotman-Dickenson, vol. 3, pp. 329–353, vol. 4, pp. 1–101.

*Primary Examiner*—Barry S. Richman
*Assistant Examiner*—Brion P. Heaney

[57] ABSTRACT

A hydrocarbon feedstock containing at least one paraffin hydrocarbon and an odor-causing impurity is deodorized by contact with a deodorizing agent. The deodorizing agent is a mixture of nickel oxide and a rare earth metal oxide and the odor-causing impurity is from the group consisting of sulfides, mercaptans, olefins, and oxygenated olefins. The feedstock is contacted with the deodorizing agent at a temperature not exceeding 150° C.

23 Claims, No Drawings

PROCESS FOR DEODORIZING A PARAFFINIC HYDROCARBON FEEDSTOCK

This invention relates to the deodorization of a paraffinic hydrocarbon-containing feedstock.

BACKGROUND

The aerosol industry has successfully employed fluorocarbons as propellants in aerosol containers. Fluorocarbons are well suited to this purpose since they are usually non-flammable, non-toxic and odorless. Use of fluorocarbons as propellants has, however, diminished because of the adverse environmental impact they are believed to have on the ozone layer of our atmosphere. As a consequence it has become desirable to find substitutes for the fluorocarbon propellants. Saturated hydrocarbons have been used to this end. Best suited are the low boiling paraffinic hydrocarbons such as, for example, propane, isobutane and pentane.

One disadvantage associated with the use of saturated hydrocarbons is the presence of impurities that impart undesirable odors. Although these impurities are usually present only in very small amounts their odorous presence is typically very perceptible. These odor-causing impurities must be removed before the hydrocarbon is used as a propellant. The odor-causing impurities include sulfides, mercaptans, olefins and oxygenated olefins. Removal of olefin impurities, for example, can be a formidable task since quantities as low as 10 parts per million (ppm) (0.001 wt %) are known to cause an unacceptable odor.

This invention provides a process for the deodorization of such hydrocarbon propellants. More broadly, the process is applicable to the deodorization of hydrocarbon feedstocks containing odor-causing impurities.

BRIEF SUMMARY OF THE INVENTION

In accordance with this invention, a paraffinic hydrocarbon-containing feedstock is deodorized by contacting the feedstock with a deodorizing agent. The deodorizing agent is a mixture of at least one oxide of nickel and at least one oxide of the rare earth metals. In an embodiment of this invention, the feedstock is fractionated after contact with the deodorizing agent.

This invention is further and more completely defined by the description which follows.

DETAILED DESCRIPTION OF THE INVENTION

The process of this invention is carried out by bringing an impurity-containing, paraffinic hydrocarbon-containing feedstock into contact with a deodorizing agent. The deodorizing agent of this invention is a mixture of (1) at least one oxide of nickel, and
(2) at least one oxide of a rare earth metal.

The nickel oxide can be, by way of non-limiting example, nickel(II) oxide (NiO). Nickel(II) oxide is commercially available to those desiring to practice this invention.

The rare earth metals are: scandium (Sc), yttrium (Y), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). The deodorizing agent of this invention includes at least one oxide of the above-identified rare earth metals. The oxide can be, for example, in the form of a sesquioxide, $M_2O_3$, where M represents a rare earth metal and O represents elemental oxygen. Examples of such sesquioxides include $Sc_2O_3$, $Y_2O_3$, $La_2O_3$, $Ce_2O_3$, $Pr_2O_3$, $Nd_2O_3$, $Pm_2O_3$, $Sm_2O_3$, $Eu_2O_3$, $Gd_2O_3$, $Tb_2O_3$, $Ho_2O_3$, $Tm_2O_3$, $Lu_2O_3$ and the like. Also included within the scope of this invention are the oxides represented by the formula $M_yO_x$ where the ratio of x to y is greater than or equal to 1.5 and less than or equal to 2.0. Examples of such oxides include $CeO_2$, $PrO_2$, $TbO_2$, $Ce_7O_{12}$, $Pr_7O_{12}$, $Tb_7O_{12}$, $Ce_9O_{16}$, $Pr_9O_{16}$, $Ce_5O_9$, $Pr_5O_9$, $Ce_{11}O_{20}$, $Pr_{11}O_{20}$, $Tb_{11}O_{20}$, $Pr_6O_{11}$ and the like. Other oxides of the rare earth metals such as the monooxides, MO, can also be employed in the practice of this invention.

In one embodiment of this invention, the rare earth metal oxide is an oxide of a lanthanide metal. The lanthanide series consists of Ce, Pr, Nd, Pm, Sm, Eu, Gd, Tb, Dy, Ho, Er, Tm, Yb and Lu.

In another embodiment of this invention, the rare earth metal oxide is an oxide of Sc, Y or La.

The reader desiring more information concerning rare earth elements and oxides thereof is referred to the following sources of information: Comprehensive Inorganic Chemistry, J. C. Bailar, Jr., H. J. Emeleus, Sir Ronald Nyholm and A. F. Trotman-Dickenson, Volume 3, pages 329-353 and Volume 4, pages 1-101 and the Kirk-Othmer Encyclopedia of Chemical Technology, Third Edition, Volume 19, pages 833-854. Numerous other sources of information are readily available.

It is preferred to use the mixture of nickel and rare earth oxides in combination with a support. The use of a support is preferred because it facilitates handling of the deodorizing agent and provides more effective contact with the hydrocarbon feedstock. Examples of suitable supports include, but are not limited to, molecular sieves, diatomaceous earths, montmorillonite clays, silicates (Ca, Mg, etc.), silicas, alumina and the like.

Although this invention is not limited thereto, it is contemplated that a deodorizing agent comprising a support, nickel oxide and rare earth metal oxide can typically contain about 0.5 to 10 weight percent nickel oxide and about 0.5 to 15 weight percent rare earth metal oxide. The above weight percentages are calculated on the basis of the total weight of the support, nickel oxide and rare earth metal oxide.

The deodorizing agent can be regenerated after extended use by heating it at a temperature of at least about 100° C. and by contacting it with nitrogen ($N_2$) gas.

In accordance with this invention, the process is carried out by bringing an impurity-containing hydrocarbon feedstock into contact with the deodorizing agent. The hydrocarbon feedstock to be purified in accordance with this process can be any paraffinic hydrocarbon (i.e. alkane) or mixture of paraffinic hydrocarbons. Examples include methane, ethane, propane, n-butane, isobutane, any of the pentanes and other compounds (including all isomers) of the general formula $C_nH_{2n+2}$, where n is an integer signifying the number of carbon atoms. This invention is especially well suited for paraffinic hydrocarbons useful as propellants represented by the above formula wherein n is less than about 6.

Odor-causing impurities in the feedstock can include, for example, olefins (i.e. alkenes), sulfides, mercaptans and numerous other sulfur-based compounds and oxygenated compounds. Olefins are of particular concern and this invention, though not limited thereto, is especially well suited for the deodorization of olefin-containing hydrocarbon feedstocks. Of most concern are the low molecular weight (i.e. molecular weight less than about 84), odor-causing olefins. Examples of low molecular weight, odor-causing olefins include propylene, isobutylene, n-butenes, pentenes and the like. It is contemplated that in a typical hydrocarbon feedstock the weight ratio of total paraffinic hydrocarbon to total olefin will be greater than about 4 to 1 and in many cases greater than about 20 to 1. This invention, however, is not limited to the above and is applicable to other hydrocarbon feedstocks including those having a higher olefin content or no olefin at all. Paraffinic hydrocarbon feedstocks useful as propellants having a low molecular weight olefin content of less than about 1000 parts by weight per million parts by weight paraffinic hydrocarbon are especially well suited for the practice of this invention.

The feedstock can contain, in addition to paraffinic hydrocarbons and odor-causing impurities, other components which are neither paraffinic hydrocarbons nor odor-causing. Typically, but not necessarily, the content of such other compounds will be low or non-existent.

The process can be carried out in any manner and with any apparatus capable of bringing the feedstock into contact with the deodorizing agent. Persons of skill in the relevant art possess sufficient knowledge of reactor technology to practice this aspect of the invention. Information on reactor technology can be found in the Kirk-Othmer Encyclopedia of Technology, Volume 19, pages 880-913 as well as in numerous other books and references.

A vertical tubular reactor is well suited to the purposes of this aspect of the invention. The feedstock can be passed upwards or downwards, as desired, through deodorizing agent positioned in the vertical reactor. Flow through the reactor can be continuous and at steady state if desired. The rate at which feedstock is fed into the reactor will depend in part on the type of paraffinic hydrocarbon being deodorized and the type and amount of odor-causing impurities present in the feedstock. A typical feed rate is about 5 liquid volumes of feedstock per volume of deodorizing agent bed per hour or a Liquid Hourly Space Velocity (LHSV) of 5. Other typical rates include a Weight Hourly Space Velocity (WHSV) of 3.86 and a Gas Hourly Space Velocity (GHSV) of 1230. The following flow rates are considered to be within the scope of this invention (but this invention is not limited thereto):

0.5 to 200 LHSV
0.3 to 150 WHSV
100 to 50,000 GHSV.

The process described herein can be run at ambient room temperature or at lower or elevated temperatures if desired. However, temperatures above about 150° C. are not recommended.

The process described herein can be carried out in either liquid or vapor phase but liquid phase is preferred. To conduct the process in the liquid phase it may be necessary to operate under a slight pressure particularly with the lower boiling paraffinic hydrocarbons. For example, when propane is being treated a pressure of 130-150 psig (0.896-1.034 MPa) may be necessary to maintain a liquid phase. When isobutane is the feedstock, a pressure of about 40-60 psig (0.27-0.41 MPa) may be necessary to maintain a liquid phase.

After contact with the deodorizing agent the product (i.e. the treated feedstock) can be passed to a distillation column or some other fractionation or separation means to recover purer paraffinic hydrocarbon. It is believed that olefin contact with the deodorizing agent produces a higher molecular weight material. This increase in molecular weight facilitates separation (as by distillation for example) from the paraffinic hydrocarbon.

The following examples are given to provide a better and more complete disclosure of this invention but should not be interpreted to limit its scope.

EXAMPLE I

This example describes a typical catalyst preparation whereby NiO and a rare earth like CeO is deposited on a support. This general procedure is also described in U.S. Pat. No. 4,217,248 column 7, line 49 to column 8, line 41. Two hundred grams of 13X molecular sieve (Davison Chem Co., grade 544, 8-12 mesh) was treated at ambient room temperature under a current of flowing air of ambient humidity (30 to 70%) for two days to obtain a partially hydrated catalyst. The mole sieve material was placed in a tubular glass reactor equipped with heating means and inlet and outlet means for cation exchange solutions. An aqueous cation exchange solution of 400 grams $NH_4Cl$, 200 grams $NiCl_2.xH_2O$ and 100 grams $CeCl_3.xH_2O$ (Alfa Chem. Co.) in 4 liters of deionized water was prepared. The partially hydrated mole sieve was wetted with a portion of the above solution and charged to the tubular glass reactor. The remainder of the aqueous solution was then pumped through the mole sieve at a rate of about 142 mL per hour. The temperature in the cation exchange zone was about 95° C. The aqueous solution was pumped continuously through the catalyst for about 48 hours to effect complete ion exchange. A total of 2640 mL of solution was collected at the exit end of the tubular reactor. After cooling, the material was filtered and washed 6 times with 500 mL portions of deionized water and air dried to give 512 grams of catalyst. The impregnated mole sieve material was calcined by heating to about 95° C. overnight followed by heating at 500° C. for about 8 hours. The catalyst thus prepared contained an estimated 4.6 wt. % nickel oxide and 9.6 wt. % cerium oxide.

EXAMPLE II

This example describes a procedure used to evaluate the effectiveness and utility of deodorizing agents. A comparison of five different samples, each representing a different composition of matter, is provided. The samples tested are described below:

Sample A: 100 wt. % 13X molecular sieve support.

Sample B: 95 wt. % 13X molecular sieve support. 5 wt. % nickel oxide. (This sample was made by treating the molecular sieve with an aqueous solution of 5 wt. % $NiCl_2$, 10 wt. % ammonium chloride and 85 wt. % water in a manner similar to the procedure of Example I.)

Sample C: 85.8 wt. % 13X molecular sieve. 4.6 wt. % nickel oxide. 9.6 wt. % lanthanum oxide. (This sample was made by treating the molecular sieve with an aqueous solution of 400 grams $NH_4Cl$, 200 grams $NiCl_2.xH_2O$ and 100 grams $LaCl_3.xH_2O$ in a manner similar to the procedure of Example I.)

Sample D: 85.8 wt. % 13X molecular sieve. 4.6 wt. % nickel oxide. 9.6 wt. % mixture of rare earth oxides (on a weight percentage basis, the mixture was about 23% lanthanum oxide, 43.5% cerium oxide, 5.4% praseodymium oxide, 17.9% neodymium oxide, 1.9% samarium oxide, 0.6% gadolinium oxide and 7.7% others.) (This sample was made by treating the molecular sieve with an aqueous solution of rare earth chlorides sold by American Potash Corp. in a manner similar to the procedure of Example I.)

Sample E: 85.8 wt. % 13X molecular sieve. 4.6 wt. % nickel oxide. 9.6 wt. % cerium oxide. (This sample was prepared in accordance with Example I.)

The nickel oxide of the above samples is believed to have been primarily nickel(II) oxide, NiO. The rare earth oxides are believed to have been primarily sesquioxides of the formula $M_2O_3$ and/or oxides of the formula $M_yO_x$ where $1.5 \leq x/y \leq 2.0$. M is generically representative of the rare earth elements.

Each sample was tested in the following manner to determine its effectiveness in eliminating odor-causing olefins from a hydrocarbon feedstock. A bed of deodorizing agent was formed in a stainless steel tubular reactor (outside diameter=2.5 cm, length=53.5 cm) by charging 37.2 grams of the sample to the reactor. A slow stream of nitrogen gas was passed through the deodorizing agent bed for 3 hours at 177° C. (350° F.) to activate the deodorizing agent. Afterwards, the reactor and its contents were cooled to ambient room temperature. An isobutane feedstock containing 132 parts per million (ppm) olefin was passed through the deodorizing agent bed at about 5 LHSV. A slight nitrogen pressure of about 35 psig was maintained on the bed.

The effluent product exiting from the reactor was periodically (every half hour after about 1 or 2 hours after start-up) analyzed by gas-liquid chromatography (GLC) to determine low molecular weight olefin content. The GLC was conducted at 50° C. using a 60 cm³ per minute helium flow through a 0.635 cm×9.135 meter column packed with 19% bis[2(2-methylethoxy)ethyl]ether. The introduction of feedstock into the reactor and the analysis of effluent product continued until the presence of olefin in the effluent product was detected. The effectiveness of each sample is reported as the ratio of feed volume to bed volume. The feed volume is the volume of hydrocarbon feedstock that was passed into the reactor prior to the detection of olefin in the effluent product. The bed volume is the volume of the deodorizing agent bed in the reactor. The results for each sample are reported below.

Sample A: Analysis of the product effluent within 1 hour of start-up indicated no reduction in olefin content of the feedstock after treatment. Therefore, the feed volume to bed volume ratio was 0. It is concluded that 13X molecular sieves alone are ineffective as deodorizing agents.

Sample B: Analysis of the product effluent first detected the presence of olefin after about 32.5 hours. The feed volume to bed volume ratio was calculated to be about 160.

Sample C: Obtained a feed volume to bed volume ratio of about 160.

Sample D: Obtained a feed volume to bed volume ratio of about 490.

Sample E: Obtained an initial feed volume to bed volume ratio of about 1422. The deodoriz- reactor at 950° F. for 12 hours. After regeneration about 890 volumes of feedstock per volume of deodorizing agent bed was passed through the reactor without detection of olefins. The run was discontinued at this point even though no olefins had been detected.

The results are summarized in Table I below.

TABLE I

| Deodorizing Agent | Feed Volume to Bed Volume Ratio |
|---|---|
| Sample A | 0 |
| Sample B | 160 |
| Sample C | 160 |
| Sample D | 490 |
| Sample E | 1422 |
| Sample E (regenerated) | 890+[a] |

[a]Run discontinued even though olefin not detected.

These examples demonstrate the utility of Samples B, C, D and E in eliminating low molecular weight olefins. After the above-described treatment (i.e., contact with the deodorizing agent), the treated feedstock can be passed to a separation means (e.g., distillation column) for recovery of a purer paraffinic hydrocarbon product.

We claim:

1. A deodorization process comprising contacting a feedstock with a deodorizing agent at a temperature not exceeding about 150° C.; wherein said feedstock is comprised of at least one paraffin hydrocarbon and contains an odor-causing impurity; wherein said odor-causing impurity is selected from the group consisting of sulfides, mercaptans, olefins and oxygenated olefins; and wherein said deodorizing agent is comprised of a mixture of
   (i) at least one oxide of nickel, and
   (ii) at least one oxide of a rare earth metal.

2. A process in accordance with claim 1 wherein said contacting is carried out at ambient room temperature.

3. A process in accordance with claim 1 wherein said deodorizing agent is regenerated by heating said deodorizing agent to a temperature of at least about 100° C. in the presence of nitrogen gas.

4. A process in accordance with claim 1 wherein said impurity is an olefin.

5. A process in accordance with claim 4 wherein said olefin is an odor-causing olefin having a molecular weight of less than about 84; and wherein said paraffinic hydrocarbon is represented by the formula $C_nH_{2n+2}$ where n is less than about 6.

6. A process in accordance with claim 5 wherein the total low molecular weight, odor-causing olefin content of said feedstock is less than about 1000 parts by weight per million parts by weight of total paraffinic hydrocarbon in said feedstock.

7. A process in accordance with claim 5 wherein said feedstock after contact with said deodorizing agent is passed to a separation means for recovery of paraffinic hydrocarbon.

8. A process in accordance with claim 7 wherein said separation means is a distillation column.

9. A process in accordance with claim 1 wherein said deodorizing agent is further comprised of a support; and wherein said mixture of said oxides is supported by said support.

10. A process in accordance with claim 9 wherein said support is a molecular sieve support.

11. A process in accordance with claim 9 wherein said rare earth metal is selected from scandium, yttrium and lanthanum.

12. A process in accordance with claim 9 wherein the deodorizing agent is comprised of about 0.5 to 10 weight percent nickel oxide and about 0.5 to 15 weight percent rare earth metal oxide wherein the above weight percentages are calculated on the basis of the total weight of the support, nickel oxide and rare earth metal oxide.

13. A process in accordance with claim 9 wherein said nickel oxide is nickel(II) oxide.

14. A process in accordance with claim 9 wherein said rare earth metal oxide is an oxide of a lanthanide metal.

15. A process in accordance with claim 14 wherein said lanthanide metal oxide is a sesquioxide of the formula $M_2O_3$ wherein M represents a lanthanide metal.

16. A process in accordance with claim 14 wherein said lanthanide metal oxide is represented by the formula $M_yO_x$ wherein M represents a lanthanide metal and the ratio of x to y is greater than or equal to 1.5 and less than or equal to 2.0.

17. A process in accordance with claim 14 wherein said lanthanide metal oxide is an oxide of cerium.

18. A process in accordance with claim 9 wherein said impurity is an olefin; wherein the weight ratio of total paraffinic hydrocarbon to total olefin in said feedstock is greater than about 20 to 1; and wherein said feedstock after contact with said deodorizing agent is passed to a separation means for recovery of paraffinic hydrocarbon.

19. A process in accordance with claim 18 wherein said rare earth metal oxide is cerium oxide.

20. A process in accordance with claim 19 wherein said separation means is a distillation column, and wherein said feedstock and said deodorizing agent are contacted in a tubular reactor.

21. A process in accordance with claim 20 wherein said support is a molecular sieve support.

22. A deodorization process consisting essentially of contacting a feedstock with a deodorizing agent; wherein said feedstock consists essentially of at least one paraffin hydrocarbon and contains an odor-causing impurity; wherein said odor-causing impurity is selected from the group consisting of sulfides, mercaptans, olefins and oxygenated olefins; and wherein said deodorizing agent consists essentially of a mixture of (i) at least one oxide of nickel, and (ii) at least one oxide of rare earth metal.

23. A process in accordance with claim 22 wherein said contacting is carried out at a temperature not exceeding about 150° C.

* * * * *